United States Patent
Stringer et al.

(10) Patent No.: US 6,497,877 B1
(45) Date of Patent: Dec. 24, 2002

(54) PLASMINOGEN ACTIVATOR AS AN ANTI-INFLAMMATORY AGENT

(75) Inventors: Kathleen A. Stringer, Denver, CO (US); Brooks M. Hybertson, Boulder, CO (US); John E. Repine, Englewood, CO (US); Joe M. McCord, Denver, CO (US)

(73) Assignee: University Technology Corporation, Boulder, CO (US)

( * ) Notice: Subject to any disclaimer, the term of this patent is extended or adjusted under 35 U.S.C. 154(b) by 0 days.

(21) Appl. No.: 09/355,522

(22) PCT Filed: Jan. 29, 1998

(86) PCT No.: PCT/US98/01948

§ 371 (c)(1), (2), (4) Date: Oct. 22, 1999

(87) PCT Pub. No.: WO98/32459

PCT Pub. Date: Jul. 30, 1998

Related U.S. Application Data

(60) Provisional application No. 60/036,566, filed on Jan. 27, 1997.

(51) Int. Cl.$^7$ .................. A61K 38/48; A61K 38/49; A61K 38/00
(52) U.S. Cl. ................ 424/94.64; 424/94.63; 435/212; 435/226; 514/2; 514/826; 514/851; 514/886; 514/887
(58) Field of Search .............. 424/94.64, 94.63; 435/212, 226; 514/2, 826, 851, 886, 887

(56) References Cited

U.S. PATENT DOCUMENTS 5,556,621 A    9/1996    Kawauchi et al. ....... 424/94.64

OTHER PUBLICATIONS

Ord et al. Imaging of Thrombi with Tissue–type Plasmingen Activator Rendered Enzymatically Inactive and Conjugated to a Residualizing Label. Circulation (1992) 85, No. 1: 288–297.*

Stringer, "Tissue Plasminogen Activator Inhibits Reactive Oxygen Species Production by Macrophages," Pharmacotherapy 2000;20(4):375–379.

Appella et al. "The Receptor–binding Sequence of Urokinase" The Journal of Biological Chemistry vol. 262, No. 10, Issue of Apr. 5, pp. 4437–4440, 1987.

Bell et al. "Inflammatory response, neutrophil activation, and free radical production after acute myocardial infarction: effect of thrombolytic treatment" BR Heart J 1990;63:82–7.

Davidow et al. "Mutations affecting the activity of urokinase–type plasminogen" Protein Engineering vol. 4 No. 8 pp. 923–928. 1991.

Felez et al. "Binding of Tissue Plasminogen Activator to Human Monocytes and Monocytoid Cells" Blood, vol. 78, No. 9 (Nov. 1), 1991: pp 2318–2327.

Guidot et al. "Inhaled nitric oxide prevents neutrophil–mediated, oxygen radical–dependent leak in isolated rat lungs" The American Physiological Society 1040–0605/95 1995.

Gurewich et al. "Characterization of the Intrinsic Fibrinolytic Properties of Prourokinase through a Study of Plasmin–resistant Mutant Forms Produced by Site–specific Mutagenesis of Lysine" The American Society of Clinical Investigation, Inc. vol. 82, Dec. 1988, 1956–1962.

Hart et al. "Regulation of Plasminogen Activators and Their Inhibitors in Rheumatic Diseases: New Understanding and the Potential for New Directions" The Journal of Rheumatology 1989; 1184–1191.

Loscalzo et al. "Tissue plasminogen Activator" Medical Intelligence Drug Therapy vol. 319 No. 14 925–931.

Madison et al. "Converting Tissue Plsminogen Activator to a Zymogen: A Regulatory Triad of Asp–His–Ser" Science vol. 262 Oct. 15, 1993 419–421.

Mehta et al. "Tissue Plasminogen Ac tivator And Plasmin Independently Decrease Human Neutrophil Activation" Life Sciences, vol. 45, pp. 1665–1669 Printed in the USA.

Mickelson et al. "Protection of Myocardial Function and Coronary Vasculature by Streptokinase" Journal of Cardiovascular Pharmacology 12:186–195 1988 Raven Press, Ltd,. New York.

Ny et al. "The structure of the human tissue–type plasminogen activator gene: Correlation of intron and exon structures to functional and structural domains" Proc. Natl. Acad. Sci. USA vol. 81, pp 5355–5359, Sep. 1984 Biochemistry.

Pennica et al. "Cloning and expression of human tissue–type plasminogen activator cDNA in *E. coli*" Nature vol. 301 Jan. 20, 1983 214–221.

Riccio et al. "The human urokinase–plasminogen activator gene and its promoter" Nucleic Acids Research vol. 13 No. 8 1985 2759–2771.

Riesenberg et al. "Inhibition of superoxide production in human neutrophils by combinations of herparin and thrombolytic agents" BR Heart 1995; 73: 14–19.

Smith III et al. "Reduction of Myocardial Ischemic/Reperfusion Injury and Neutrophil Accumulation After Therapeutic Administration of Streptokinase" Journal of Cardiovascular Pharmacology 18: 729–738 1991 Raven Press, Ltd., New York.

(List continued on next page.)

*Primary Examiner*—Christopher S. F. Low
*Assistant Examiner*—Holly Schnizer
(74) *Attorney, Agent, or Firm*—Pillsbury Winthrop LLP; Robin L. Teskin

(57) ABSTRACT

Plasminogen activator acts as an anti-inflammatory agent by inhibiting generation of superoxide anion by a mechanism that is not related to L-arginine, is not dependent on thrombolytic activity, and is not a function of oxygen free radical scavenging. Moreover, in in vivo models of inflammation, treatment with plasminogen activator reduces edema without inhibiting neutrophil infiltration in in vivo models of inflammation.

7 Claims, 9 Drawing Sheets

OTHER PUBLICATIONS

ACCP 1994 Annual Meeting Abstracts p349.

Stringer et al. "Antiinflammatory Activity of Tissue Plasminogen Activator in the Carrageenan Rat Footpad Model" Free Radical Biology & Medicine, vol. 22. No. 6, pp. 985–988, 1997 pp. 985 and 987 only.

Stringer et al. "Tissue Plasminogen Activator (tPA) Inhibits Human neutrophil Superoxide Anion Production in Vitro" Inflammation. vol. 21. No. 1. 1997 27–34.

Stringer et al. "Tissue Plasminogen Activator (tPA) Inhibits Interleukin–1 Induced Acute Lung Leak" Free Radical Biology & Medicine, vol. 25, No. 2, pp. 184–188, 1998.

Sutton et al. "Principles of Thrombolytic Therapy In Myocardial Infarction" Cardiovascular Pharmacology and Therapeutics 1992 pp. 481–498.

Stringer et al. Effect of streptokinase, tissue plasminogen activator, and anistreplase on rat footpad edema. Pharmacotherapy 1994; 14:349.

Lindenfeld et al. Streptokinase and t–PA reduce neutrophil oxygen radical generation in vitro. Circulation Oct. 1991; 84 (suppl. II):ll–84.

* cited by examiner

PLASMINOGEN ACTIVATOR AS AN ANTI-INFLAMMATORY AGENT

This application is the national phase of international application PCT/US98/01948 filed Jan. 29, 1998 under 35 U.S.C. 371 which designated the U.S. This application also claims the benefit of U.S. Provisional Application No. 60/036,566, filed Jan. 27, 1997.

BACKGROUND OF THE INVENTION

1. Field of the Invention

The present invention relates to the use of plasminogen activator as an anti-inflammatory agent.

2. Description of the Related Art

Plasminogen activators play an important physiological role in the regulation of thrombolysis. This action is exploited therapeutically to promote reperfusion in conditions such as, for example, acute myocardial infarction, pulmonary embolism, and thrombotic stroke.

An equilibrium between two opposing reactions, coagulation which forms blood clots and fibrinolysis which dissolves blood clots, maintains a patent and intact vascular endothelium. To stop blood loss from a leaking blood vessel, blood clots form a hemostatic plug at the site of a break in the vessel wall. But if the blood clot obstructs flow through a blood vessel, the result may be, for example, a myocardial infarction, a pulmonary embolism, or a thrombotic stroke.

The interruption of flow through the blood vessel will lead to tissue ischemia. In this condition, the tissue is deprived of oxygen and becomes jeopardized, a state in which the tissue is injured but still potentially viable. If however the hypoxic condition is maintained for a period of several hours, the tissue becomes necrotic and cannot recover. It is therefore important that reperfusion, the restoration of blood flow, be accomplished as soon as possible to minimize tissue necrosis. However, even if reperfusion is accomplished before tissue necrosis occurs, leukocytes may become activated and infiltrate the jeopardized tissue. Consequently, reperfusion only leads to partial recovery of jeopardized tissue, the remainder being permanently damaged by leukocyte mediated oxidative injury or other pathophysiological mechanisms (Hansen, Circulation 91:1872–1885, 1995).

In particular, patients with acute myocardial infarction have significantly reduced mortality when treated with a plasminogen activator. This benefit is due to blood clot fibrinolysis and timely opening of the infarct-related artery. However, once the infarct-related artery is patent, neutrophils can contribute to the reperfusion injury that accompanies reversal of ischemia. Reperfusion of the myocardium is associated with neutrophil activation and infiltration. The nature of the neutrophil-mediated injury is not fully characterized but is in part due to the production of superoxide anion ($O_2^-$) and/or related oxidative products. This principle (activation of white blood cells release of toxic mediators and resultant pathophysiology in the host) is common to many inflammatory diseases including, but not limited to, acute respiratory distress syndrome, cystic fibrosis, asthma, arthritis, and nephritis.

A drawback of thrombolytic therapy with plasminogen activator is the increased incidence of stroke and intracerebral hemorrhage in treated patients. The generation of fibrin fragments and depletion of fibrinogen caused by the exogenous plasminogen activator is a direct cause of excessive bleeding disorders.

Side-effects of existing anti-inflammatory agents such as steroidal (e.g., corticosteroids) and non-steroidal (e.g., aspirin, acetaminophen, ibuprofen) drugs include growth retardation, osteoperosis, gastric and renal toxicity, and adrenal suppression. In addition, these agents can impair the healing process due to inhibition of neutrophil infiltration by steroidal and non-steroidal drugs. Most non-steroidal drugs are also limited to oral formulations.

We have now found that plasminogen activator can reduce tissue injury by acting as an anti-inflammatory agent. More generally, plasminogen activator reduces tissue damage due to leukocyte mediated oxidative injury. Plasminogen activator inhibits leukocyte generation of oxygen radicals (e.g., hydroxides, peroxides, superoxides) by a mechanism that is independent of thrombolytic activity and scavenging of oxygen free radicals. By separating the thrombolytic and the anti-inflammatory functions of plasminogen activator, the present invention provides a method of reducing tissue damage due to oxidative injury (e.g., reperfusion injury) while mitigating complications from excessive bleeding, such as stroke and intracerebral hemorrhage. Moreover, because the present invention does not inhibit neutrophil migration and infiltration, use of plasminogen activator as an anti-inflammatory agent will not interfere with processes mediated at least in part by neutrophils such as, for example, wound healing or tissue remodeling, which is a shortcoming of existing steroidal and non-steroidal anti-inflammatory agents.

SUMMARY OF THE INVENTION

It is an object of the invention to reduce cell and/or tissue damage due to oxidative injury.

It is a further object of the invention to inhibit oxidant production by leukocytes.

Another object of the invention is to use plasminogen activator as an anti-inflammatory agent.

Yet another object of the invention is to treat a human or animal afflicted with an inflammatory disease.

It is an object of the invention to select and/or develop derivatives of plasminogen activator that retain the anti-inflammatory property of plasminogen activator.

Another object of the invention is to provide a derivative of plasminogen activator that can be used as an anti-inflammatory agent.

Yet another object of the invention is to provide a non-thrombolytic form of plasminogen activator useful as an anti-inflammatory agent.

In one embodiment of the invention, a plasminogen activator or derivative thereof is administered to an organism, and thereby reduces oxidative injury to tissue of the organism. Preferably, the organism is afflicted with an autoimmune disease or an inflammatory disease. The organism may be a human or an animal. The oxidative injury may be mediated by an inflammatory cell (e.g., neutrophil, macrophage, monocyte, eosinophil, mast cell, basophil). Tissue at risk of oxidative injury may include, but is not limited to, any blood-prefused tissue (e.g., myocardiun, lung, brain) or any bone or joint.

In a second embodiment of the invention, a plasminogen activator or derivative thereof is applied to an inflammatory cell (e.g., neutrophil, macrophage, monocyte, eosinophil, mast cell, basophil), and thereby reduces oxidant production by the inflammatory cell.

A third embodiment of the invention is the treatment of an organism afflicted with an inflammatory disease by administering a plasminogen activator or derivative thereof, and thereby reducing or alleviating a symptom of the disease caused by inflammation. The organism may be a human or an animal. Preferably, the organism is afflicted with an acute or chronic inflammatory disease.

A fourth embodiment of the invention is the prophylactic treatment of an organism at risk for development of an inflammatory illness by administering a plasminogen activator or derivative thereof, and thereby preventing onset of the illness or reducing the severity of a symptom of the illness. The organism may be a human or an animal. Preferably, the organism is at risk for development of an acute or chronic inflammatory illness.

For the above embodiments of the invention, plasminogen activator may be tissue-plasminogen activator (tPA), urokinase (uPA), reteplase (rPA), or a derivative thereof. Such plasminogen activators may be termed "endogenous plasminogen activators" to distinguish them from streptokinase. Tissue plasminogen activator and urokinase are "mammalian plasminogen activators" whereas streptokinase is produced by bacteria. For these two definitions, no distinction is made between native protein and recombinantly produced protein (e.g., non-glycosylated). Instead, "endogenous" may mean derived from the species of the organism or the inflammatory cell being treated and "mammalian" indicates the gene encoding the plasminogen activator is derived from a mammal.

Preferred derivatives of endogenous plasminogen activator have the property of reduced fibrinolytic activity, binding a receptor for plasminogen activator, inhibiting oxidant production, inhibiting leukocyte activation, or a combination thereof. More preferably, the derivative of endogenous plasminogen activator binds urokinase receptor with increased affinity, reduces production of superoxide anion by an inflammatory cell (e.g., neutrophil, macrophage, monocyte, eosinophil, mast cell, basophil), reduces release of other mediators of inflammation (e.g., arachidonate metabolites, cytokines, histamine, monokines, nitric oxide, proteases, serotonin) by an inflammatory cell or the endothelium, or a combination thereof. The 15 Kd amino-terminal fragment (ATF) (amino acid residues 1–135) of urokinase is an example of such a derivative, binding the urokinase receptor but lacking fibrinolytic activity.

A fifth embodiment of the invention is to provide structural variants of an endogenous plasminogen activator, to screen the structural variants for their ability to reduce inflammation, and to select those structural variants which reduce inflammation. The structural variant may be produced recombinantly, by peptide synthesis, by protease cleavage, or by chemical modification. Preferred structural variants have the property of reduced fibrinolytic activity, binding a receptor for plasminogen activator, inhibiting oxidant production, inhibiting leukocyte activation, or a combination thereof. The 15 Kd amino-terminal fragment (ATF) (amino acid residues 1–135) of urokinase is an example of such a preferred structural variant, binding the urokinase receptor but lacking fibrinolytic activity. More preferably, the structural variant binds the receptor for plasminogen activator with increased affinity, reduces production of oxidant radicals and/or another marker of leukocyte activation, reduces cellular degranulation, reduces vascular permeability, or a combination thereof.

Endogenous plasminogen activator may be tissue-plasminogen activator (tPA), urokinase (uPA), or a derivative thereof. A plasminogen derivative with reduced fibrinolytic activity is preferred, but not necessary. A plasminogen activator derivative that binds the plasminogen activator receptor on leukocytes, thereby inhibiting production of oxidants and/or other markers of leukocyte activation, is also preferred but not necessary.

The advantages of the invention include the ability to inhibit inflammation and tissue injury using a plasminogen activator that does not cause excessive bleeding, and provision of a novel class of anti-inflammatory agents that reduces tissue injury caused by leukocyte production of oxidants and proteases, without interfering with other leukocyte functions such as, for example, migration and infiltration.

DETAILED DESCRIPTION OF THE INVENTION

Figure 1:
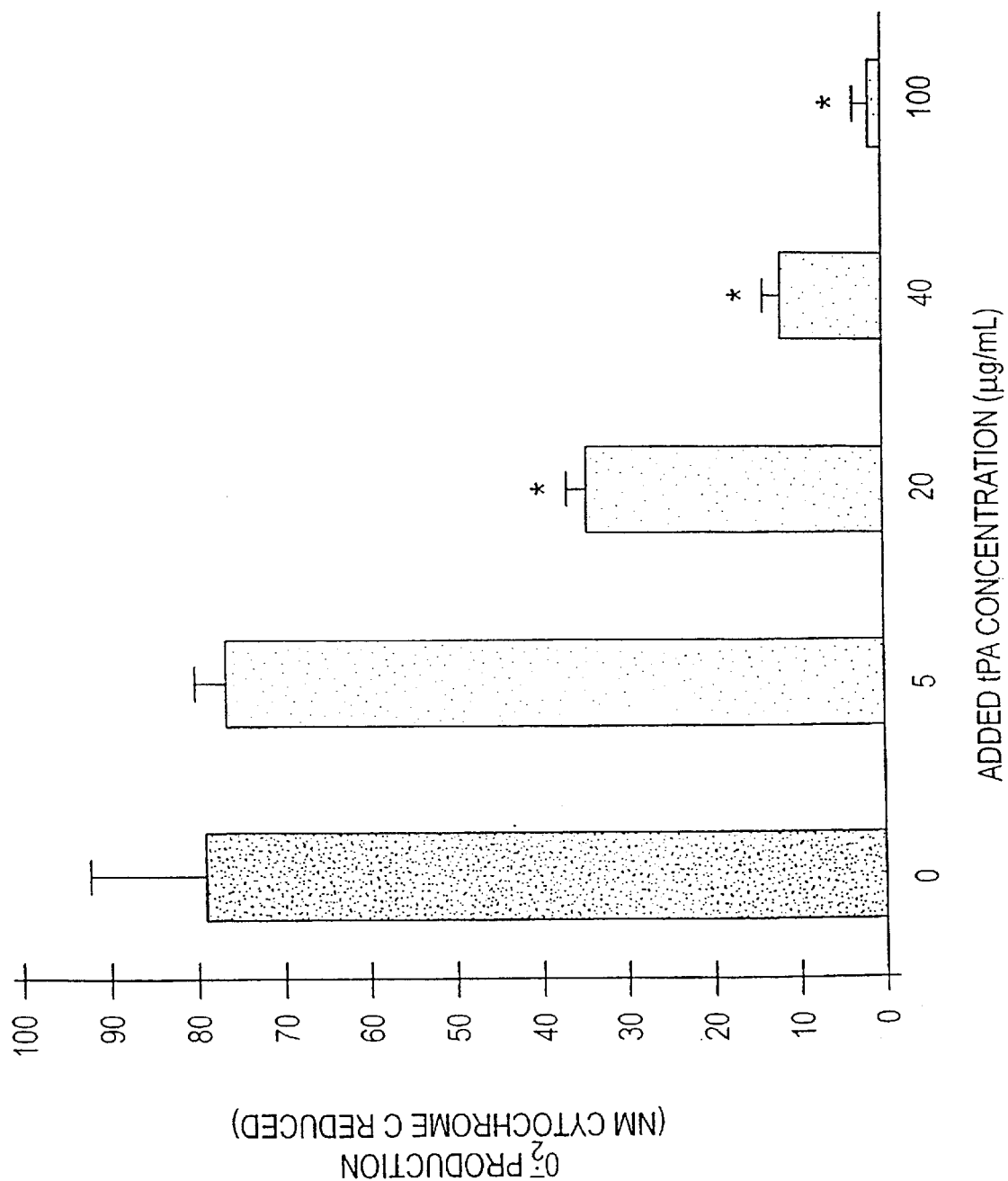
FIG. 1 shows the effect of tPA on $O_2^-$ production by human neutrophils stimulated with PMA in vitro. Adding tPA concentrations of 20–100 µg/ml significantly (asterisk represents $p<0.05$) reduced neutrophil $O_2^-$ production compared to values obtained following no additions or addition of 5 µg/ml tPA. Each value is the mean±standard error of three or more determinations.

Blood coagulation is a complex process consisting of interactions of various blood components which eventually gives rise to a fibrin network, or blood clot. Degradation of the fibrin network can be accomplished by activation of the zymogen plasminogen to plasmin. Plasmin is a serine protease which acts directly to degrade the fibrin network and thereby regulate the coagulation process. Conversion of plasminogen into plasmin is normally catalyzed in vivo by tissue plasminogen activator (tPA), a fibrin-specific serine protease which is believed to be the physiological vascular activator of plasminogen. Urokinase plasminogen activator (uPA) is another member of the class of plasminogen activators characterized as serine proteases. tPA and uPA are functionally and immunologically distinguishable (reviewed in "Thrombolytic Agents" by Collen et at. and "Principles of Thrombolytic Therapy in Myocardial Infarction" by Sutton et al., in Singh et al., Eds., Cardiovascular Pharmacology and Therapeutics).

Tissue Plasminogen Activator

Human tPA is a multidomain serine protease secreted by vascular endothelial cells. Five distinct structural domains make up the 527 amino acids of the active human tPA protein. The DNA and amino acid sequences of human tPA was described by Pennica et al. (Nature 301:214–221, 1983). The numbering system employed by Pennica et al. is used herein. The gene encoding tPA is comprised of 12 exons split by introns (Ny et al., Proc. Natl. Acad. Sci. USA 81:5355–5359, 1984). These introns correspond, in part, to the junction of the domains described below.

The amino-terminal portion of the molecule contains a disulfide-linked loop referred to as the Finger (F) domain (amino acid residues 1–43). This domain is highly homologous to the Finger domain of fibronectin and provides this molecule with fibrin-binding properties. The second domain, called the Epidermal Growth Factor-like (EGF) domain (amino acid residues 44–91), is highly homologous with epidermal growth factor. Similar EGF domains occur in serine proteases such as protein C, clotting factors VII, IX and X, and urokinase. The third and fourth domains are highly disulfide-linked structures referred to as Kringles K1 and K2 (amino acid residues 92–173 and 180–261, respectively). Similar kringle structures are present in plasma proteins such as prothrombin, plasminogen, and urokinase and are also believed to be important in binding fibrin. The fifth domain, located at the carboxy-terminus, is the Serine Protease (SP) domain (amino acid residues 262–527) The SP domain is homologous to similar domains in plasma clotting serine proteases, urokinase, and trypsin, and contains the active site for the fibrin-specific serine protease activity (amino acid residues $His^{322}$, $Asp^{371}$, and $Ser^{478}$).

The precursor form of tPA additionally comprises a pre-region followed downstream by a pro-region, which are collectively referred to as the "pre-pro" region. The pre-region contains a signal peptide which is important for protein secretion of tPA by cells. The pre-sequence is believed responsible for secretion of tPA into the lumen of the endoplasmic reticulum, a necessary step in extracellular secretion. The pro-sequence is believed to be cleaved from the tPA molecule following transport from the endoplasmic reticulum to the Golgi complex.

tPA usually circulates as a single polypeptide chain of $M_r$ approximately 72 Kd, which is converted to a two-chain form by cleavage of the peptide bond cleavage between $Arg^{275}$ and $Ile^{276}$. The heavy chain of tPA (two variants of $M_r$ 40 Kd and 37 Kd) is derived from the amino-terminus, while the light chain ($M_r$ 33 Kd) is derived from the carboxy-terminal end of the tPA molecule. This cleavage is catalyzed by trypsin or plasmin, and is accompanied by an increase in activity, as measured using synthetic substrates, and by an increase in fibrinolytic activity. Single-chain tPA becomes active upon binding to fibrin, probably due to a conformational change in the activator induced by binding to fibrin. Recombinant tPA (i.e., alteplase) is provided as a one-chain polypeptide that is cleaved in vivo to an active two-chain polypeptide.

The gene and protein for tPA, methods of assaying for various properties of tPA, methods of making derivatives and structural variants of tPA, methods of expressing and purifying tPA, and other information are described in U.S. Pat. Nos. 4,766,075, 4,963,357, 5,094,953, 5,106,741, 5,108,901, 5,149,533, 5,156,969, 5,232,847, 5,242,688, 5,246,850, 5,270,198, 5,275,946, 5,486,471, and 5,556,621, incorporated herein by reference.

Urokinase and Receptor for Plasminogen Activator uPA is released from many types of cultured cells as a single-chain proenzyme with little or no plasminogen activating capacity. By limited proteolysis with catalytic amounts of plasmin, this proenzyme can be converted to its active two-chain counterpart. The proenzyme nature of single-chain uPA is also reflected in the finding that it has essentially no amidolytic activity with synthetic substrates, and that it has little or no reactivity with macromolecular inhibitors and synthetic inhibitors.

In the intact organism, pro-uPA is the predominant form of uPA in intracellular stores, and it also constitutes a sizable fraction of the uPA in extracellular fluids. Extracellular activation of pro-uPA is therefore be a crucial step in the physiological regulation of the uPA pathway of plasminogen activation. The plasmin-catalyzed activation of pro-uPA provides a positive feedback mechanism that accelerates and amplifies the effect of activation of a small amount of pro-uPA. However, plasmin-resistant single-chain derivatives of urokinase do have fibrinolytic activity (Gurewich et al., J. Clin. Invest. 82:1956–1962, 1988).

The urokinase molecule exists is several biologically active forms: high molecular weight (54 Kd) and low molecular weight (33 Kd), each composed of single-chain or two-chain material; the low molecular weight form is derived from the high molecular weight form by enzymatic cleavage of the peptide bond between $Lys^{158}$ and $Ile^{159}$. Human uPA is encoded by a gene with 11 exons and has an N-terminal Epidermal Growth Factor-like (EGF) domain implicated in receptor binding (mainly exon IV) and a single Kringle domain (exons V and VI), followed by a Serine Protease (SP) domain (exons VII–XI) for a polypeptide of 411 amino acids (Riccio et al., Nucl. Acids Res. 13:2759–2771, 1985). The active site comprises amino acid residues $His_{204}$, $Asp^{255}$, and $Ser^{356}$. The numbering system of Riccio et al. is used herein.

The cellular receptor for uPA (uPAR) is found on cells such as leukocytes (Felez et al., Blood 78:2318–2327, 1991; Min et al., J. Immunol. 148:3636–3642, 1992; Plesner et al., Am. J. Clin. Path. 102:835–841, 1994). Human uPAR has been characterized and cloned (Roldan et al., EMBO J. 9:467–474, 1990) as a 55–60 Kd glycoprotein. The receptor binds active 54 Kd uPA, its single polypeptide chain proenzyme, pro-uPA as well as 54 Kd uPA inhibited by the active site reagent DFP, but shows no binding of the 33 Kd form of active uPA. Thus, binding to the receptor does not require the catalytic site of uPA, and in agreement with these findings, the binding determinant of uPA has been identified in the amino-terminal part of the enzyme, in a region which in the primary structure is remote from the catalytic site. The receptor binding domain is located in the 15 Kd amino-terminal fragment (ATF) (amino acid residues 1–135) of uPA (Stoppelli et al., Proc. Natl. Acad. Sci. USA 82:4939–4943, 1985), more precisely within the EGF domain (Appella et al., J. Biol. Chem. 262:4437–4440, 1987). The uPA amino acid residues which appear to be critical for receptor binding are located within amino acid residues 12–32 (Appella et al., ibid.; Magdolen et al., Eur. J. Biochem. 237:743–751, 1996); the peptides described by Appella et al. and Magdolen et al. may be used to demonstrate the correlation between receptor binding and the anti-inflammatory activity of plasminogen activator.

The gene and protein for uPA and uPAR, methods of assaying for various properties of uPA and uPAR (e.g., ligand-receptor binding), methods of making derivatives and structural variants of uPA and uPAR, methods of expressing and purifying uPA and uPAR, and other information are described in U.S. Pat. Nos. 4,326,033, 4,370,417, 5,112,755, 5,175,105, 5,219,569, 5,240,845, 5,472,692, 5,519,120, 5,550,213, and 5,571,708 incorporated herein by reference.

Proteins have been defined by means of determined DNA sequence and deduced amino acid sequence; it will be understood that natural allelic variation may exist within a species.

The above tPA or uPA protein may be obtained from natural sources; produced by recombinant techniques in bacteria, yeast, or mammalian cells; and/or synthesized chemically. Derivatives and structural variants of tPA or uPA proteins may be produced by chemical or proteolytic cleavage of the native protein, peptide synthesis, and/or recombinant techniques. Such derivative and structural variants may be generated by random mutagenesis; domain swapping, deletion, or duplication; and/or directed mutagenesis. Derivatives and structural variants of tPA or uPA proteins may contain amino acid substitutions, deletions, additions and/or replacements. The molecular interaction between substrate and enzyme (U.S. Pat. Nos. 5,433,940 and 5,464,820, incorporated herein by reference), or ligand and receptor (Wells, Bio/Technology 13:647–651, 1995 and U.S. Pat. No. 5,534,617, incorporated herein by reference) may also be used to design derivatives and structural variants of tPA or uPA. Protein may be fractionated and purified by its physical and/or chemical characteristics (Janson and Ryder, Protein Purification, VCH, New York, 1989; Scopes, Protein Purification, Springer-Verlag, New York, 1993).

Non-thrombolytic forms of plasminogen activator may be produced by means such as, for example, incubation with a serine protease inhibitor as described in U.S. Pat. No. 5,304,482 incorporated herein by reference, formation of a complex with a plasminogen activator inhibitor (PAI), isolation of a plasminogen activator fragment after chemical or enzymatic cleavage, and/or genetic engineering. The proteolytic activity of tPA can be inhibited by PPACK. The tPA-PPACK complex retained its ability to inhibit human neutrophil $O_2^-$ production in vitro (Stringer et al., Inflammation 21:27–34, 1997). A derivative of plasminogen activator may be expressed by recombinant DNA technology (Goeddel, Gene Expression Technology, Academic Press, San Diego, 1990; Kriegler, Gene Transfer and Expression, Stockton Press, New York, 1990; Ausubel et al., Current Protocols in Molecular Biology, Wiley, New York, 1996); such derivatives may contain deletions in the serine protease (SP) domain, and/or mutations that reduce or eliminate the serine protease activity of plasminogen activator. After treatment to inactivate the protease activity of plasminogen activator, the plasminogen activator derivative may be isolated by fractionating the treated plasminogen activator and assaying for fractions containing an activity which inhibits oxidant production by leukocytes.

The compounds of the invention may be formulated according to known methods to prepare pharmaceutical compositions, whereby the plasminogen activator or derivative thereof is combined with a pharmaceutically acceptable carrier vehicle. Suitable vehicles and their formulation are described, for example, in Remington's Pharmaceutical Sciences by E. W. Martin. Such compositions will contain an effective amount of the plasminogen activator or derivative thereof together with a suitable amount of vehicle in order to prepare pharmaceutically acceptable compositions suitable for administration to a human or animal. Formulations or other delivery systems (e.g., liposomes) will be suitable for oral, topical, inhalation, or parenteral administration.

Compositions of the invention may include an inhibitor of a protease released during inflammation by leukocytes (e.g., cathepsin G, chymase, elastase, tryptase), an oxidant scavenger (e.g., superoxide dismutase, see for example U.S. Pat. No. 4,976,959, incorporated herein by reference), a growth factor (see for example U.S. Pat. No. 5,057,494, incorporated herein by reference) and/or an inhibitor of interleukin-1 (U.S. Pat. Nos. 5,075,222, 5,359,032, 5,453,490, 5,455,330, and 5,521,185, incorporated herein by reference), in addition to plasminogen activator or a derivative thereof. Leukocyte proteases and inhibitors are described in U.S. Pat. Nos. 5,420,110, 5,541,288, 5,455,229, 5,510,333, and 5,525,623, incorporated herein by reference. Compositions of the invention may include a protease inhibitor such as, for example, $\alpha_1$-antiprotease, $\alpha_1$-antitrypsin (AAT), aprotinin, 3,4-dichloro-isocoumarin, diisopropyl fluorophosphate (DFP), $\alpha_2$-macroglobulin, phenylmethylsulfonyl fluoride (PMSF), plasminogen activator inhibitor (PAI), secretory leukoprotease inhibitor (SLPI), and/or urinary trypsin inhibitor (UTI), in addition to plasminogen activator or a derivative thereof.

An effective amount of a compound of the invention may depend upon a number of factors including, for example, the age and weight of the human or animal, the precise condition requiring treatment and its severity, and the route of administration. The precise amount will ultimately be at the discretion of the attending physician or veterinarian. Thus, practice of the present invention may involve any dose, combination (with another plasminogen activator or other agents), reformulation, or delivery system (e.g., liposomes) for oral, topical, inhalation, or parenteral administration.

Intravascular infusions are normally carried out with the parenteral solution contained within an infusion bag or bottle, or within an electrically operated infusion syringe. The solution may be delivered from the infusion bag or bottle to the patient by gravity feed or by the use of an infusion pump. The use of gravity feed infusion systems does not afford sufficient control over the rate of administration of the parenteral solution and, therefore, the use of an infusion pump is preferred especially with solutions containing relatively high concentrations of plasminogen activator or derivative thereof. Plasminogen activator. or a derivative thereof may also be orally ingested, topically applied, or inhaled as an aerosol.

The invention provides methods of administering a plasminogen activator derivative to reduce oxidative injury, administering a plasminogen activator derivative as an anti-inflammatory agent, applying a plasminogen activator derivative to reduce oxidant production by a neutrophil, and applying a plasminogen activator or derivative thereof to reduce oxidant production by a macrophage, monocyte, eosinophil, mast cell, or basophil. The production of oxidants by inflammatory cells may be measured by cytochrome C reduction, chemiluminescence, or fluorescence detection. Neutrophil function may be assayed by a variety of means (e.g., Bell et al., Br. Heart J. 63:82–87, 1990; Riesenberg et al., Br. Heart J. 73:14–19, 1995; Guidot et al., Am. J. Physiol. 13:L2–L5, 1995). The role of oxidants in causing tissue injury is reviewed by Janssen et al. (Lab. Invest. 69:261–274, 1993) and Jaeschke (Proc. Soc. Exp. Biol. Med. 209:104–111, 1995).

In general, proteins (e.g., cytokines, monokines, receptors, proteases) may be measured by bioassay, ligand-receptor binding, immunoassay, and/or Western blotting. Histamine may be measured by fluorescence.(Shore et al., J. Pharmacol. Exp. Ther. 127:182–186, 1959). Nitric oxide may be measured by chemiluminescence (Hybertson et al., Anal. Lett. 27:3081–3093, 1994). Proteases (e.g., elastase) may also be measured using a labeled peptide substrate (e.g., Barnett et al., J. Surg. Res. 63:6–10, 1996). Moreover, serotonin, arachidonate metabolites (e.g., prostaglandins, leukotrienes), cellular degranulation, and vascular permeability may be measured using assays well known in the art (see Handbook of Experimental Inmmunology).

Inflammatory diseases such as acute lung injury, acute respiratory distress syndrome, arthritis, asthma, bronchitis, cystic fibrosis, hepatitis, inflammatory bowel disease, multiple sclerosis, reperfusion injury (e.g., myocardial), nephritis, pancreatitis, psoriasis, artery occlusion (e.g., retinal), stroke, systemic lupus erythematosus, transplantation, ultraviolet light induced injury, and/or vasculitis may be treated using the invention. The inflammatory disease may be acute or chronic, and is preferably mediated by leukocytes (reviewed in Weissmann et al., Ann. N.Y. Acad. Sci. 389:11–24, 1982; Janoff, A., Annu. Rev. Med. 36:207–216, 1985; Hart et al., J. Rheumatol. 16:1184–1191, 1989; Doring, Am. J. Respir. Crit. Care Med. 150:S114–S117, 1994; Demling, Annu. Rev. Med. 46:193–202, 1995).

The invention also provides a method of screening structural variants of plasminogen activator for their ability to act as anti-inflammatory agents. Activity as an anti-inflammatory agent may be assayed by oxidant production by an inflammatory cell (e.g., neutrophil, macrophage, monocyte, eosinophil, mast cell, basophil); the carrageenan rat footpad model; and/or interleukin-1 induced pulmonary injury. In addition, structural variants of plasminogen activator may be screened for fibrinolytic activity and/or binding to a receptor for plasminogen activator.

All books, articles, applications, and patents cited in this specification are incorporated herein by reference in their entirety. This includes the priority document U.S. Appln. No. 60/036,566 filed Jan. 29, 1997. Such references are also cited as indicative of the skill in the art.

The following examples are meant to be illustrative of the present invention, however the practice of the invention is not limited or restricted in any way by them.

EXAMPLE 1

Plasminogen Activator Inhibits Oxidant Production

The following example was published after the filing date of the priority document as Stringer et al. (Inflammation 21:27–34, 1997).

Recovery and Purification of Human Neutrophils

Human neutrophils were isolated from the whole blood of a single, healthy, drug-free donor using a percoll density gradient (Polymorphprep from Nycomed, Oslo, Norway) (Ferrante and Thong, J. Immunol. Meth. 36:109, 1994). Cells were then suspended in Krebs-Ringers-Phosphate-Dextrose (KRPD) buffer (serum-free), counted, and assessed for viability using trypan blue exclusion. Tissue plasminogen activator (tPA, alteplase from Genentech, South San Francisco, Calif.) was reconstituted following the manufacturer's instructions using sterile water for injection to produce a final concentration of 1 mg/ml. All experiments were performed at 37° C. and pH 7.4, under sterile conditions. Measurement of Neutrophil $O_2^-$ Generation by tPA tPA was added to the neutrophil suspension in sufficient quantities to produce final concentrations of 5, 20, 40, or 100 $\mu$g/ml. The effect of L-arginine on neutrophil $O_2^-$ generation was also evaluated because L-arginine is a precursor of nitric oxide (NO) and the standard formulation of tPA contains 700 mg L-arginine/20 mg tPA. L-arginine (Sigma Chemical Co., St. Louis, Mo.) concentrations of 175, 700, 1400, or 3500 $\mu$g/ml were evaluated that corresponded to the tPA concentrations used above. Release of $O_2^-$ by neutrophils ($5\times10^6$ cells/ml) stimulated with phorbol myristate acetate (PMA, 1.25 $\mu$g/ml) was determined during a 30 min incubation in the absence or presence of each concentration of tPA or L-arginine. $O_2^-$ generation was determined spectrophotometrically by measuring superoxide dismutase (SOD) inhibitable horse heart ferricytochrome C reduction (Babior et al., J. Clin. Invest. 52:741–744, 1973; Fantone et al., Biochem. Biophys. Res. Comm. 113:506–512, 1983). Experiments were performed in triplicate.

PPACK Inhibition of tPA

D-Phe-Pro-Arg-chloromethyl ketone HCl (PPACK, Calbiochem, San Diego, Calif.), is an irreversible serine protease inhibitor, that inhibits the proteolytic activity of tPA in vitro (Lijnen et al., Thromb. Res. 34:431–437, 1984). tPA was incubated in the presence of PPACK at varying molar ratios (PPACK:tPA: 5:1, 25:1, 100:1, or 1000:1) for 10 min after which PPACK:tPA complexes or tPA alone (100 $\mu$g/ml) were incubated with plasminogen (375 $\mu$g/ml) for 5 hr in a cell incubator (5% $CO_2$ in air) at 37° C. Subsequently, 50 $\mu$l of each of the incubated samples were subjected to 7.5% acrylamide gel electrophoresis along with tPA (100 $\mu$g/ml), plasminogen (375 $\mu$g/ml), and plasmin (1 U/ml). Each gel was run at 30V for 16 hr and protein bands were visualized by Coomasie blue stain. The effect of the PPACK:tPA complex on human neutrophil $O_2^-$ production was also examined. Briefly, the cell suspension ($5\times10^6$ cells/ml) was divided into four groups: tPA (100 µg/ml); PPACK:tPA (5:1); PPACK (140 µM) alone, and PPACK vehicle (10 mM acetic acid). Cells (250 µl of $5\times10^6$/ml) from each group were then plated into a 96-well microtiter plate and incubated for 30 min at 37° C. in a cell incubator. Cells were then exposed to PMA (1.25 µg/ml) so that the following conditions were met (in triplicate): tPA alone, tPA+PMA, PPACK-:tPA alone, PPACK:tPA+PMA, PPACK alone, PPACK+PMA, PMA alone, PPACK vehicle, and cells alone. The plate was then incubated for an additional 30 min at 37° C. in a cell incubator after which it was placed in a plate reader (Spectramax, Molecular Devices, Menlo Park, Calif.) and $O_2^-$-production was measured as cytochrome C reduction (550 nm OD) every five min for 2 hr (Waud et al., Arch. Biochem. Biophys. 169:695–701, 1975). The kinetic disposition of each treatment was compared.

Measurement $O_2^-$ of Scavenging by tPA

The ability of tPA to scavenge $O_2^-$ was determined by measuring reduction of cytochrome C during a 30 min incubation with purified xanthine oxidase (1.6 U/ml) and hypoxanthine in the presence or absence of tPA (concentrations previously mentioned) (Waud et al., ibid.). Experiments were performed in triplicate.

Analyses of Data

The mean and standard error of the mean (±SEM) for data were determined for each experiment. Treatment groups were compared to each other and to positive and negative controls by analyses of variance and unpaired student's t tests. Concentration dependent effects were assessed by linear regression followed by an F test for significance. A p value of less than 0.05 was considered significant.

Effect of tPA on Neutrophil $O_2^-$ Generation In Vitro

Figure 2:
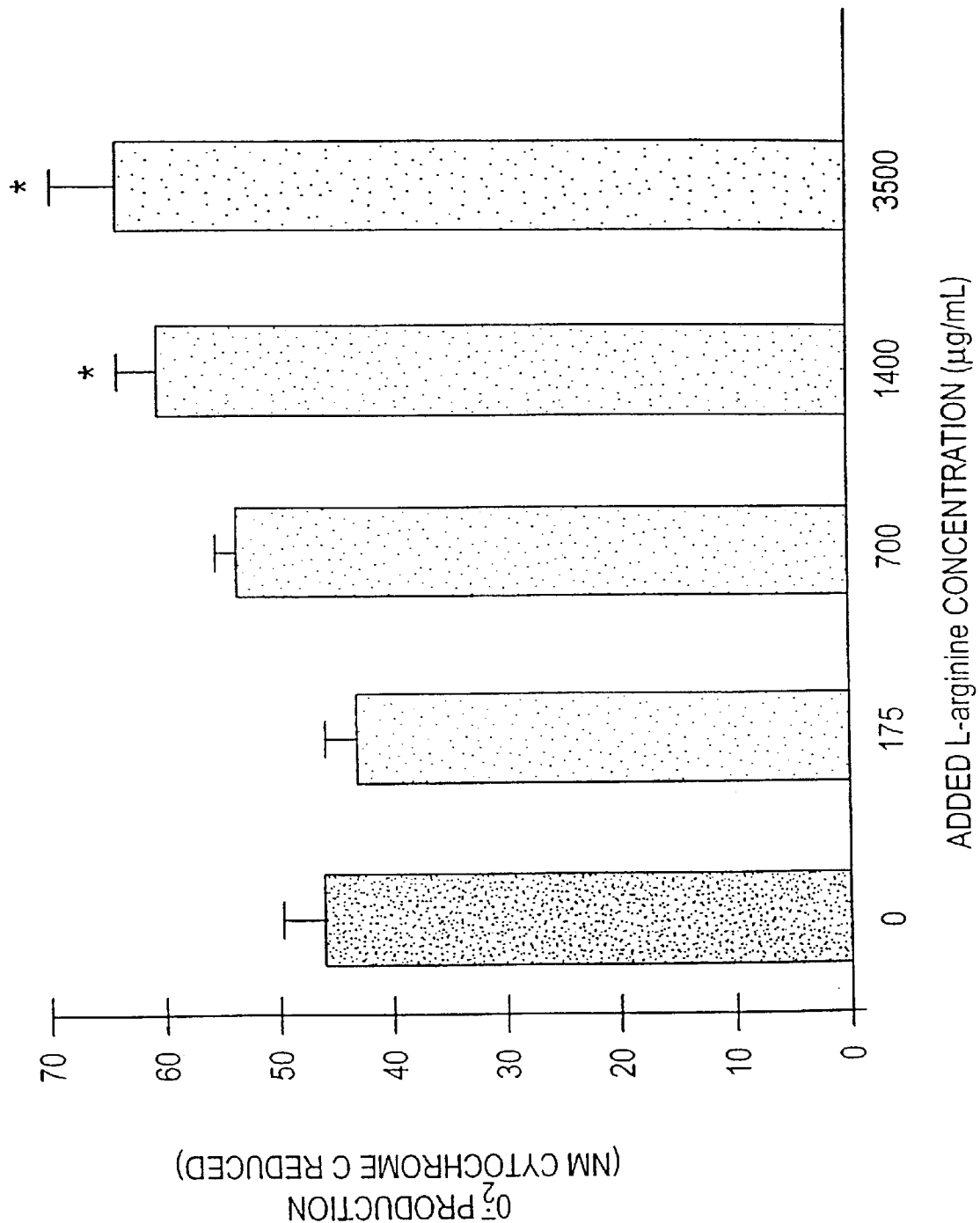
FIG. 2 shows the effect of L-arginine on $O_2^-$ production by human neutrophils in vitro. Adding 175 or 700 µg/ml of L-arginine, a component of the tPA preparation, did not decrease ($p>0.05$) $O_2^-$ production by PMA stimulated neutrophils in vitro. By comparison, adding 1400 or 3500 µg/ml of L-arginine increased (asterisk represents $p<0.05$) $O_2^-$ production by PMA stimulated neutrophils in vitro. Each value is the mean±standard error of three or more determinations.

Adding increasing amounts of tPA significantly ($p<0.025$) and progressively decreased $O_2^-$ production by human neutrophils stimulated by PMA in vitro (FIG. 1). In contrast, adding L-arginine, a component of the tPA formulation, did not decrease ($p>0.05$) $O_2^-$ production by neutrophils stimulated with PMA (FIG. 2). Neither tPA nor L-arginine altered neutrophil $O_2^-$-production by unstimulated neutrophils.

Figure 3:
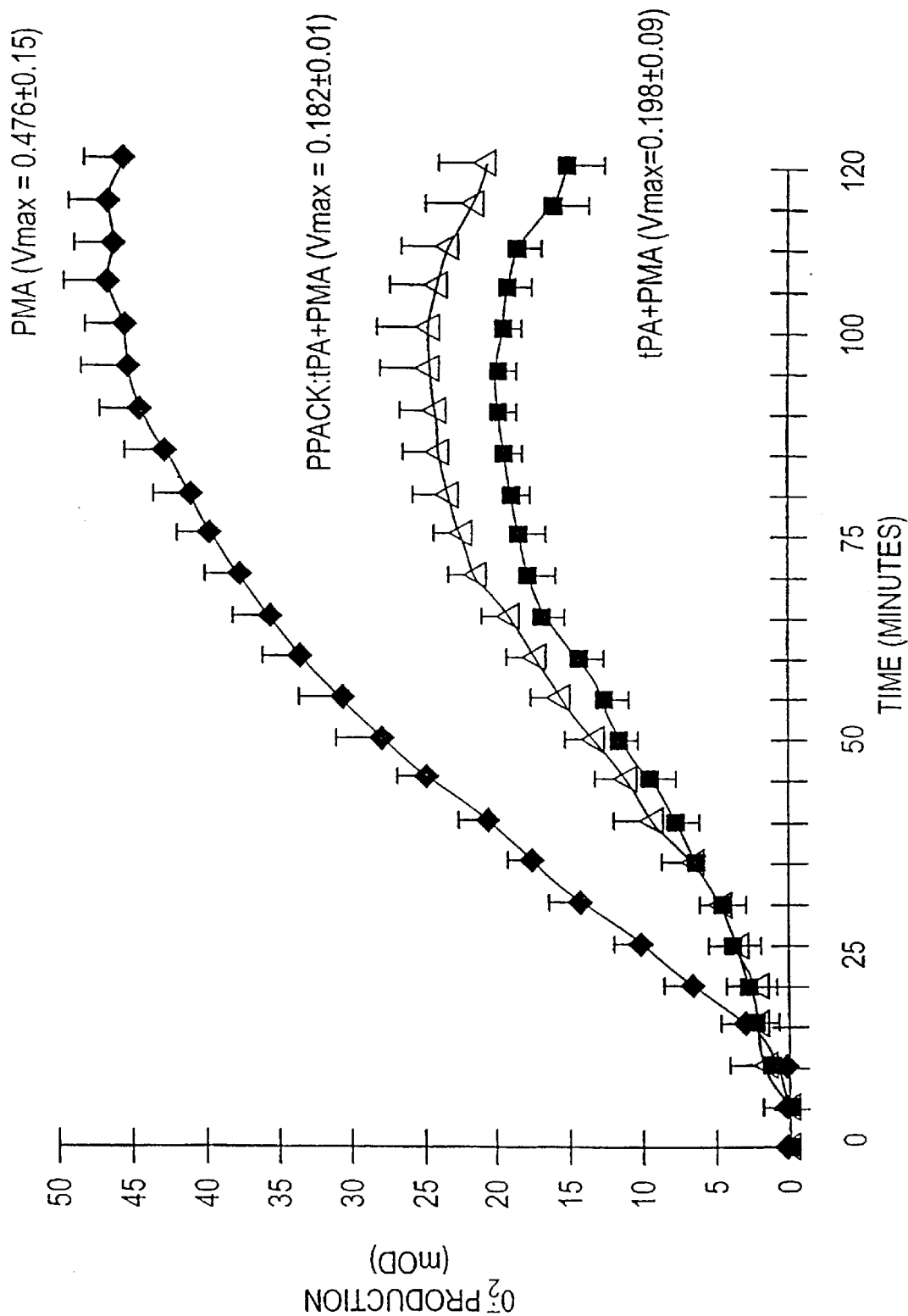
FIG. 3 shows the effect of tPA or PPACK treated tPA on $O_2^-$ production by neutrophils in vitro. Compared to PMA alone, neutrophils treated with tPA or PPACK treated tPA had comparable ($p>0.05$) decreases in $O_2^-$ generation. Neutrophils were pretreated with tPA, PPACK, or PPACK:tPA (5:1 mole ratio) and subsequently activated by PMA. The time course of cytochrome C reduction ($O_2^-$ production) was monitored by changes in optical density (mOD). Neither neutrophils alone, tPA alone, PPACK alone, or acetic acid (PPACK vehicle) altered cytochrome C reduction. The Vmax (mOD/min) or rate of cytochrome C reduction was significantly less for both tPA+PMA, filled square (0.198±0.09), and PPACK:tPA+PMA, open triangle (0.182±0.01), when compared to PMA alone, filled diamond (0.476±0.15) with $p=0.0004$ and 0.006, respectively. In addition, there was no significant difference in Vmax between the tPA+PMA and PPACK:tPA+PMA groups ($p>0.05$). Data are means of triplicate experiments.
Figure 4:
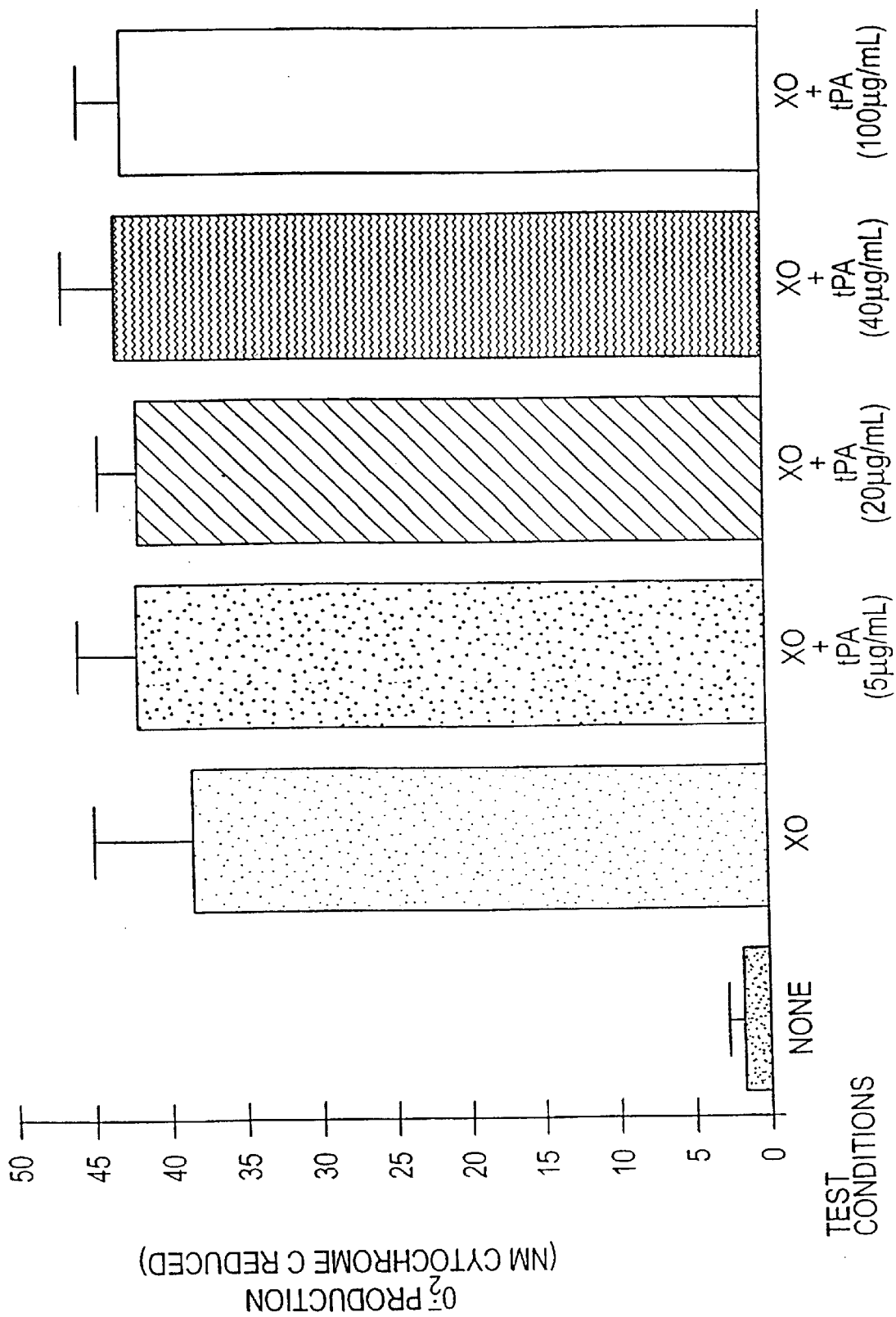
FIG. 4 shows the effect of tPA on produced by xanthine oxidase in vitro. Adding increasing amounts of tPA did not decrease ($p>0.05$) generation by xanthine oxidase (XO) in vitro. Each value is the mean±standard error of three or more experiments.

Effect of tPA Proteolytic Activity on $O_2^-$ Production tPA promoted conversion of plasminogen to plasmin. tPA mediated conversion of plasminogen to plasmin was inhibited by PPACK in a concentration dependent fashion. Based on these results, the mole:mole (PPACK:tPA) ratio used in the subsequent experiments was 5:1. In these studies, both tPA and PPACK-treated, proteolytically inactivated, tPA comparably inhibited $O_2^-$ production by neutrophils stimulated with PMA (FIG. 4). In addition, analysis of the kinetics of $O_2^-$ production showed that both tPA and proteolytically inactivated tPA decreased the Vmax of $O_2^-$ production (i.e. rate of cytochrome reduction) similarly (FIG. 3).

Effect of tPA on $O_2^-$ Generation by Xanthine Oxidase In Vitro

Adding tPA did not decrease $O_2^-$ concentrations produced by xanthine oxidase (XO) in vitro (FIG. 4).

tPA significantly reduced $O_2^-$ production by PMA stimulated human neutrophils in vitro. The inhibitory effect of tPA was not dependent on tPA proteolytic activity, not related to L-arginine in its formulation, and not a consequence of its direct scavenging of $O_2^-$. These observations show that tPA has another action, inhibition of neutrophil $O_2^-$ production, which may be used to reduce neutrophil $O_2^-$ production and prevent oxidative injury.

These results indicate that tPA acts directly on the neutrophil to reduce $O_2^-$ production, independent of fibrinolytic activity. These observations could have important clinical implications for optimizing the efficacy of tPA in the management of myocardial infarction as well as other inflammatory processes where a contribution by neutrophil derived $O_2^-$ is likely. Indeed, the possibility that tPA might have anti-inflammatory effects is supported by our related in vivo findings shown below.

EXAMPLE 2

Plasminogen Activator's Anti-Inflammatory Effect in the Carrageenan Induced Rat Footpad Model Carrageenan, a mucopolysaccharide derived from Irish sea moss, is a phlogistic agent that provokes a local antigenic inflammatory response which is primarily attributed to neutrophil mediated injury and is highly reproducible (Vinegar et al., Fed. Proc. 35:2447–2456, 1976; Vinegar et al., J. Pharmacol. Exp. Therap. 166:96–103, 1969; Vinegar et al., Eur. J. Rheumatol. Inflam; 1:204–211, 1978). This model has been used extensively to evaluate the anti-inflammatory effects of such drugs as the non-steroidal anti-inflammatory drugs, corticosteriods, and more recently superoxide dismutase (Winter and Flataker, J. Pharmacol. Exp. Therap. 150:165–171, 1965; Vinegar et al., Fed. Proc. 46:118–126, 1987; Ando et al., Biochim. Biophys. Acta 1073:374–379, 1991).

The following example was published after the filing date of the priority document as Stringer et al. (Free Radicals Biol. Med. 22:985–988, 1997).

The right hind foot volume of male Sprague-Dawley rats weighing between 200–250 grams was determined using water-displacement prior to carrageenan or carrageenan vehicle (saline) injection. Following initial baseline (pretreatment) foot volume determinations, the rats were lightly anesthetized using methoxyflurane (Pittman-Moore, Mundelcin, Ill.) and 0.10 ml of 1.5% (w/v) carrageenan (Sigma Chemical Co., St. Louis, Mo.) in sterile normal saline, or saline (0.10 ml, sterile normal saline) was injected into the plantar tissue of the right hind paw. Volume of the injected paw was measured 30 min and then every hour for 6 hr thereafter.

Treatments

Both SK and tPA were reconstituted according to manufacturers' instructions. Baseline footpad volume measurements were made immediately prior to carrageenan or saline administration.

Tissue plasminogen activator (tPA, alteplase from Genentech, South San Francisco, Calif.): Three different doses of 3, 6, and 12 mg/Kg body weight tPA were evaluated. Half of each dose was given intraperitoneally (i.p.) 10 min prior to footpad carrageenan injection. The second half of the dose was administered 2.5 hr after the first half of the tPA dose. This treatment regimen was considered necessary to account for the short half-life of tPA which is approximately 5 min (Tbbe et al., Am. J. Cardiol. 64:448–453, 1989).

L-arginine (Sigma Chemical Co., St. Louis, Mo.): The formulation of tPA (from Genentech) contains L-arginine to enhance solubility., In so far as L-arginine is a precursor of nitric oxide (NO), the effect of L-arginine on rat footpad inflammation was evaluated. Doses of L-arginine (0.1 1, 0.22, 0.44 g/Kg body weight, i.p.) utilized correspond to those contained in the tPA doses.

Streptokinase (SK, KABIKINASE® from Kabi-Vitrum, Sweden): Rats received one of three single SK doses (10, 000, 20,000, or 40,000 U/Kg body weight, i.p.) 10 min prior to the carrageenan footpad injection.

Histological Examination

Upon completion of the experiments, the animals were sacrificed and their paw removed, fixed in formalin, sectioned, and stained with hematoxylin and eosin. Sections were examined and assessed for neutrophil infiltration by an individual unaware of the treatment schemes. Neutrophils from six high powered fields (40x) of a representative slide from the highest dose of each PA treatment and the carrageenan and vehicle controls were counted and averaged.

Data Analysis

Calculation of the edema index: An edema index was calculated for each footpad as a measure of inflammation. This was determined by subtracting the weight of the water-filled tube following insertion of the paw at each time point from the weight of the water-filled tube. Edema induces a greater displacement of water. The time zero (pretreatment) foot volume was then subtracted from each time point so that changes in volume reflected those associated with edema. The mean (±SEM) edema index for each time point for each group was determined. The edema indexes for each PA or L-arginine group were compared to carrageenan control group at each time point using a Mann-Whitney two sample test. In all cases, a p value less than 0.05 was considered significant.

Histological examination: The mean (±SEM) neutrophil count per high powered field (HPF) was determined for each treatment and compared to the carrageenan control using analysis of variance (ANOVA).

Figure 5:
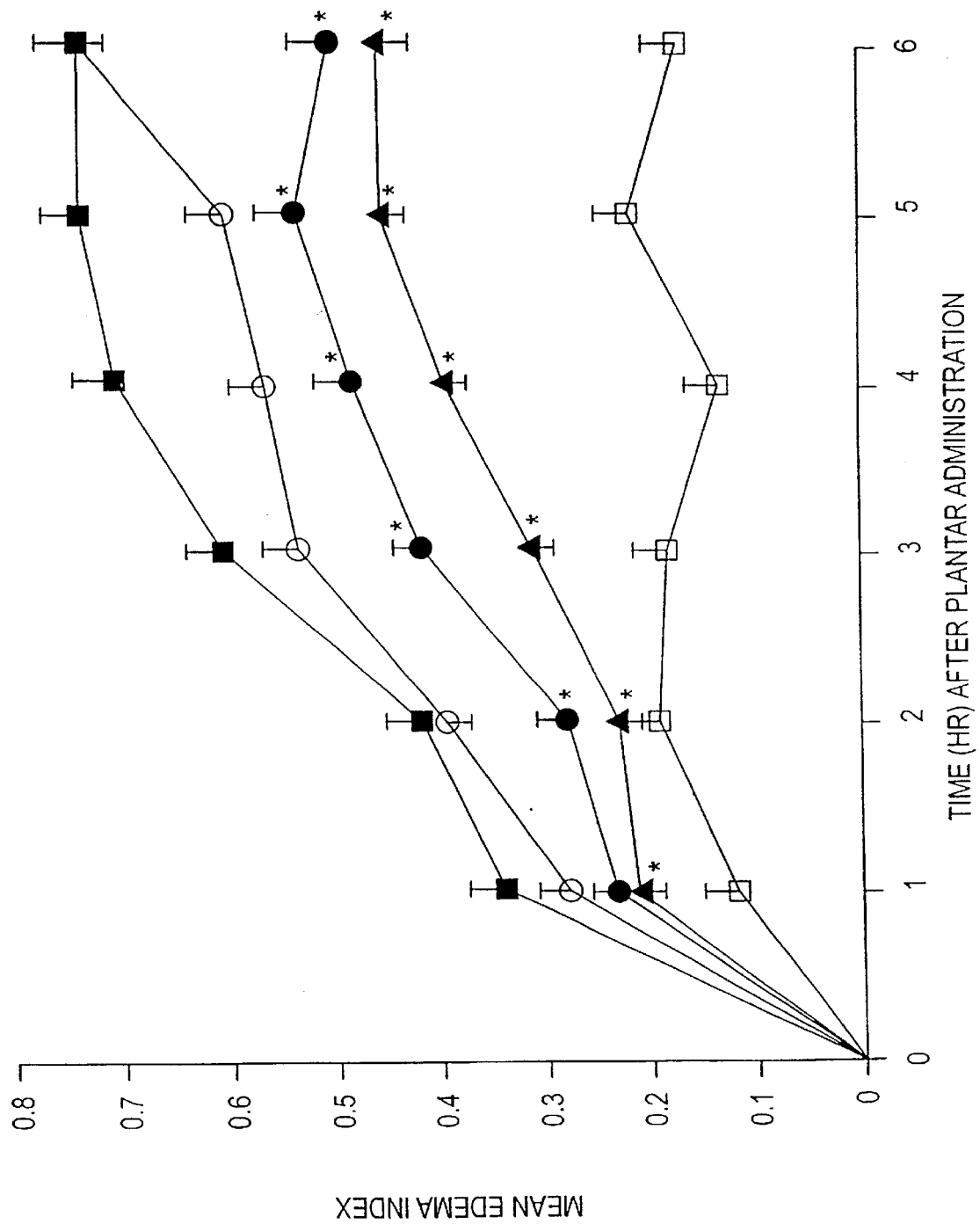
FIG. 5 shows the effect of tissue plasminogen activator (tPA) on carrageenan induced edema in rat footpad. Open square, saline alone; filled square, carrageenan alone; filled triangle, 12 mg/Kg tPA+carrageenan; filled circle, 6 mg/Kg tPA+carrageenan; open circle, 3 mg/Kg tPA+carrageenan. Edema index reflects changes in hind paw volume at different times after plantar carrageenan or saline administration. Data represent the means (±SEM) for ten experiments. Asterisk represents $p \leq 0.05$ tPA vs. carrageenan alone.
Figure 6:
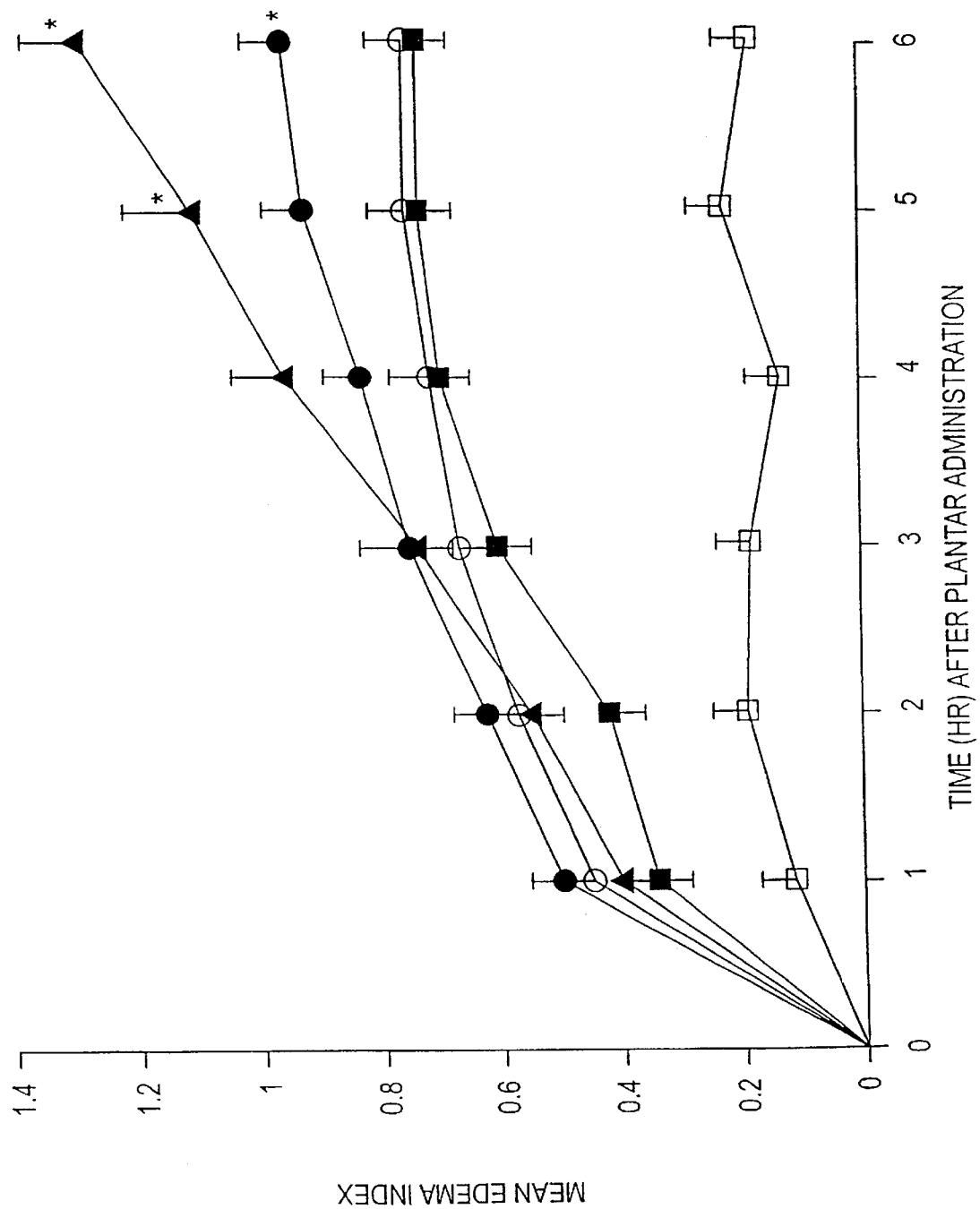
FIG. 6 shows the effect of streptokinase (SK) on carrageenan induced edema in rat footpad. Open square, saline alone; filled square, carrageenan alone; filled triangle, 40,000 U/Kg SK+carrageenan; filled circle, 20,000 U/Kg SK+carrageenan; open circle, 10,000 U/Kg SK+carrageenan. Edema index reflects changes in hind paw volume at different times after plantar carrageenan or saline administration. Data represent the means (±SEM) for ten experiments. Asterisk represents p≦0.05 for SK vs. carrageenan alone.

Carrageenan induced edema when injected into the rat footpad (FIGS. 5–6). tPA reduced edema in a dose-dependent manner (FIG. 5). At a dose of 12 mg/Kg body weight, tPA reduced edema at all time points (p<0.05) while 6 mg/body weight reduced edema beginning at the two hour time point (p<0.05); an effect that occurred prior to the second dose of tPA. The two highest doses of SK, 20,000 and 40,000 U/Kg body weight, enhanced edema at the latter time points (≦5 hr) (FIG. 6). By contrast, L-arginine, one of the constituents of the tPA formulation, had no significant effect on edema at any time.

Histological examination of the footpads revealed no significant differences in the number of neutrophils (mean+SEM) between the treatment groups and carrageenan control (carrageenan control: 30.7±0.65 cells/HPF; tPA: 35.0±12.6 cells/HPF; SK: 41.2±16.9 cells/HPF). Notably, the vehicle control footpads had no neutrophil infiltration.

This study shows that carrageenan induced inflammation can be modulated by plasminogen activator. The effect was selective in that tPA inhibited edema development while SK enhanced it. Mechanisms by which drugs can influence carrageenan induced footpad inflammation and edema include inhibition of neutrophil infiltration into the footpad, inflammatory mediator release, including neutrophil generated $O_2^-$, and/or vascular permeability. The first possibility is unlikely since there was no difference between the plasminogen activators in regard to the magnitude of neutrophil infiltration into the footpad. Generation of $O_2^-$ exerts important proinflammatory effects, including deesterification of phospholipids resulting in increased vascular permeability like that observed in ischemia-reperfusion injury (Deby et al., Biochem. Pharmacol. 39:399–405, 1990). tPA significantly reduces $O_2^-$ production by neutrophils is likely to contribute to the observed anti-inflammatory effect of tPA. The failure of L-arginine to affect edema assures that L-arginine, an excipient in the tPA formulation, does not contribute to the anti-inflammatory effect of tPA. This is consistent with our previous observation that L-arginine also does not alter neutrophil $O_2^-$ production in vitro.

Streptokinase, in contrast to tPA, enhanced inflammation as reflected in the increase in edema index at the later time points. Although it is not known whether plasminogen activators alter vascular permeability directly or indirectly via altercation of inflammatory mediator actions on endothelium, plasminogen activators have been shown to bind to endothelial cell surfaces (Hajjar et al., J. Clin. Invest. 80:1712–1719, 1987). Thus, it may be speculated that the pro-inflammatory effect of SK is due, at least in part, a direct effect on blood vessels since SK has no effect on neutrophil $O_2^-$ production. This notion is supported by the observation that SK has a vasoactive effect that is observed clinically, wherein most myocardial infarction patients treated with SK experience some degree of hypotension (a occurrence that is not observed in patients treated with tPA). Such a vasodilatory action of SK may contribute to the enhancement of edema.

EXAMPLE 3

Plasminogen Activator's Anti-Inflammatory Effect in the IL-1 Induced Pulmonary Injury Model Tissue plasminogen activator (tPA, alteplase from Genentech, South San Francisco, Calif.) was reconstituted according to the manufacturer's instructions. The total dose was 12 mg/Kg body weight given intraperitoneally (i.p.); 6 mg/Kg as administered 10 min before IL-1 and 6 mg/Kg was given 2.5 hours later. This regimen was chosen because of the short half-life of tPA (Tbbe et al., ibid.) and from the dose response study of Example 2. In addition, this dose of tPA does not increase the activated partial thromboplastin time (aPTT) in rats (Example 2; Korninger et al., Thromb. Haemost. 46:561–565, 198 1). To control for possible effects of L-arginine contained in the formulation used, a corresponding dose of L-arginine (440 mg/Kg body weight, i.p.) (Sigma Chemical Co., St. Louis, Mo.) was administered similarly.

Determination of tPA Concentration in the Lung

To determine the effect of systemic administration of tPA on lung tPA concentrations, six male Sprague-Dawley rats (300–400 gm) were given tPA as described above and then, five hours later, the lower left lobe of the lung was removed following euthanasia with methoxyflurane. Samples were stored at −80° C. until assay. Subsequently, samples were thawed and homogenized with ice-cold homogenization buffer (20 mM HEPES/glycerol buffer, pH 7.5), containing protease inhibitors (2 mM EDTA, 2 mM EGTA, 5 µg/ml aprotinin, 10 µM leupeptin, 1 mM PMSF) and centrifuged at 15,000 G for 45 min. After the protein concentration of each supernatant was determined (Lowry et al., J. Biol. Chem. 193:265–275, 1951), aliquots containing 100 µg protein were subjected to 7.5% polyacrylamide gel electrophoresis and transferred to nitrocellulose (Towbin et al., Proc. Natl. Acad. Sci. USA 76:4350–4354, 1979). These membranes were blocked with 3% skim milk in TNS buffer (15 mM Tris, pH 7.4, 150 mM NaCl, 0.1% Tween-20) overnight and then incubated with an antibody specific for tissue plasminogen activator (1:50 dilution of an anti-tPA sheep polyclonal antibody, affinity purified IgG) (Enzyme Research, South Bend, Ind.) for 60 min at 25° C. Blots were then rinsed five times for 5 min each with wash buffer (3% skim milk in TNS) and incubated with a secondary polyclonal antibody (1:10,000 dilution of rabbit anti-sheep horseradish peroxidase) (Jackson ImmunoResearch, West Grove, Pa.) for 30 min at 25° C. Following five rinses (5 min each) with wash buffer, immunoblots were visualized by application of enhanced chemiluminescence (ECL) Western blotting reagents (Pierce, Rockford, Ill.) and exposure to autoradiographic film. Immunolabeled tPA was identified by comparison to a known concentration of tPA (1 µM) run on the same gel.

Interleukin-1 Induced Acute Lung Injury

Ten minutes before intratracheal instillation of IL-1 (50 ng/0.5 ml of rhIL-1α, R&D Systems, Minneapolis, Minn.) or vehicle (0.5 ml sterile saline), tPA or L-arginine was administered to male (300–400 gm) Sprague-Dawley rats (Leff et al., Am. J. Physiol., 265:L501–L506, 1993; Leff et al., Am. J. Physiol. 266:L2–L8, 1994). The effect of L-arginine was evaluated since L-arginine, a precursor of nitric oxide synthesis in vivo, is contained in the tPA formulation that was used.

After tPA or L-arginine administration, and anesthesia with methoxyflurane (Pitman-Moore, Mundelein, Ill.), a 1 cm neck incision was made and the trachea was exposed by blunt dissection. A 25 gauge angiocath was inserted through the tracheal wall and the Teflon catheter advanced without the needle into the trachea. Saline (0.5 ml) or IL-1 (50 ng) in saline (0.5 ml) was administered followed by two 3 ml puffs of air to ensure good distal delivery of the cytokine (Leff et al., ibid.; Koh et al., J. Appl. Physiol. 79:472–478, 1995). Soft tissue was reopposed and the neck incision sutured with three interrupted 3-0 silk sutures. Five hours after IL-1α administration, lung leak, lung myeloperoxidase (MPO) activity, and lung lavage neutrophil counts were determined (Leffet al., ibid.; Krawisz et al., Gastroenterology 87:1344–1350, 1984).

Determination of Lung Leak and MPO Activity

Four and one-half hours after intratracheal instillation of saline or IL-1, rats were anesthetized with a mixture of ketamine (90 mg/Kg body weight) and xylazine (5 mg/Kg body weight) intraperitoneally and $^{125}$I-BSA (1.0 μCi in 0.5 ml) was administered intravenously. Twenty-five minutes thereafter, rats were ventilated using a Harvard small animal respirator during laparotomy, thoracotomy, and right ventricular injection of heparin (200 U in 0.2 ml). Right ventricular blood samples were obtained, lungs were perfused blood free with PBS and excised. Radioactivity in right lungs and blood samples were measured using a gamma counter. Lung leak index was estimated as counts per minute (cpm) of $^{125}$I in the lung divided by cpm in 1.0 ml of blood. Left lungs were assayed for MPO activity using o-dianiside as substrate. Six rats were utilized in the saline group (control), ten rats in the IL-1 group, and six rats in the tPA and IL-1 group.

Determination of Lung Lavage Neutrophils

Five hours after tPA administration and instillation of saline or IL-1 as described, rats were anesthetized using ketamine (90 mg/Kg body weight) and xylazine (7 mg/Kg body weight) intraperitoneally. The trachea was cannulated with an indwelling 16 gauge stub adaptor tube, and then saline (two×3.0 ml) was injected slowly and withdrawn (to lavage lungs). Recovered lavage fluid was centrifuged (250 G for 5 min) and the cell pellet resuspended in 1.0 ml of lavage supernatant; red blood cells were lysed using hypotonic saline. Total leukocytes were counted using a Coulter counter and cytospin preparations of the cells were Wright-Giemsa stained to determine the percentage and total number of neutrophils. Ten rats were utilized in the IL-1 alone and tPA+IL-1 experiments, while six rats were in the saline group (control).

Data Analysis

Data were analyzed using a one-way analysis of variance with a Student-Newman-Keuls test of multiple comparisons. A p value of less than 0.05 was accepted as being statistically significant.

Figure 7:
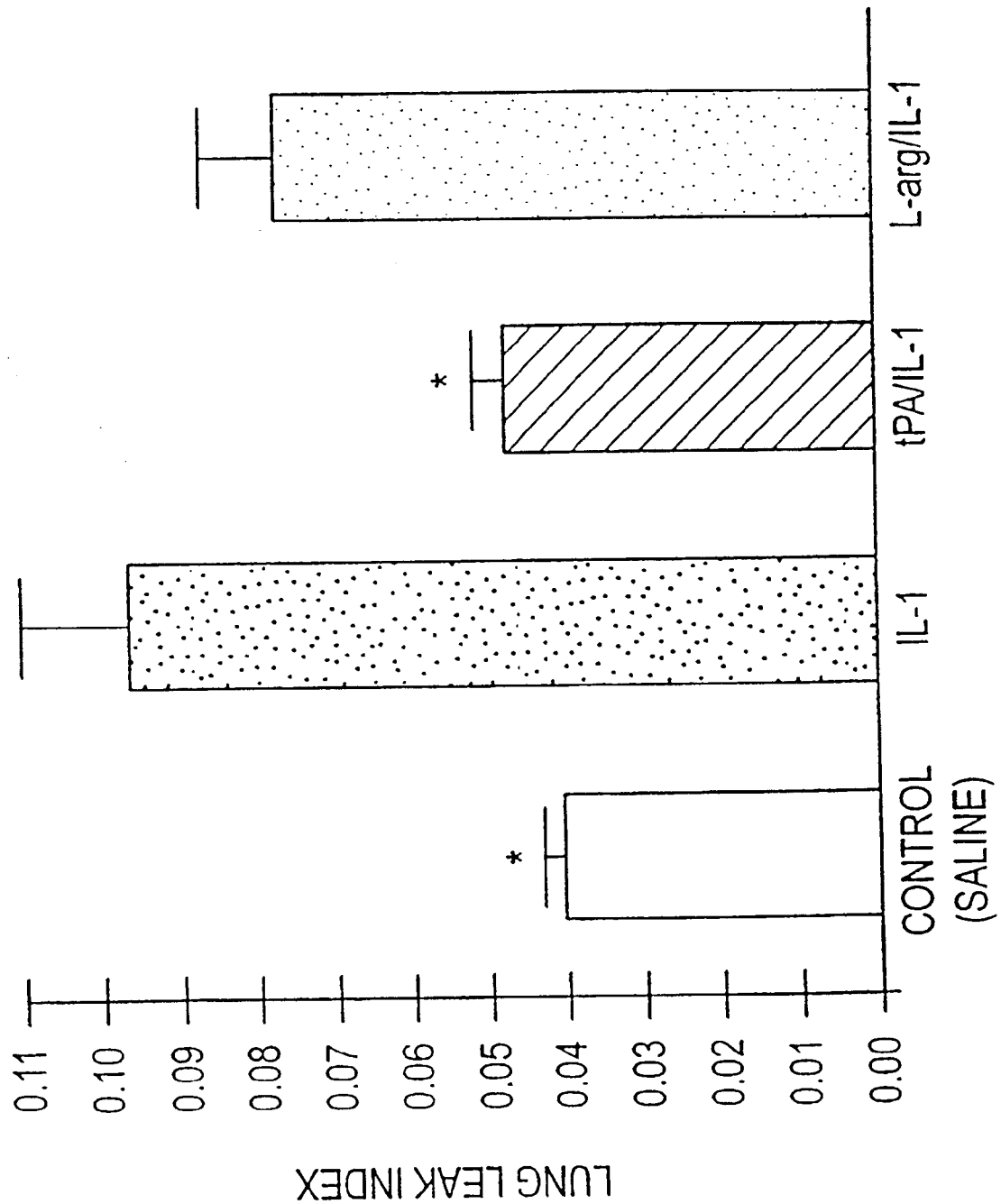
FIG. 7 shows modulation of IL-1 induced lung leak. Data are presented as the means±SEM. Asterisk represents a p value of <0.05 vs. IL-1 control group. Lung leak induced by L-arginine was not significantly different that that induced by saline alone.
Figure 9:
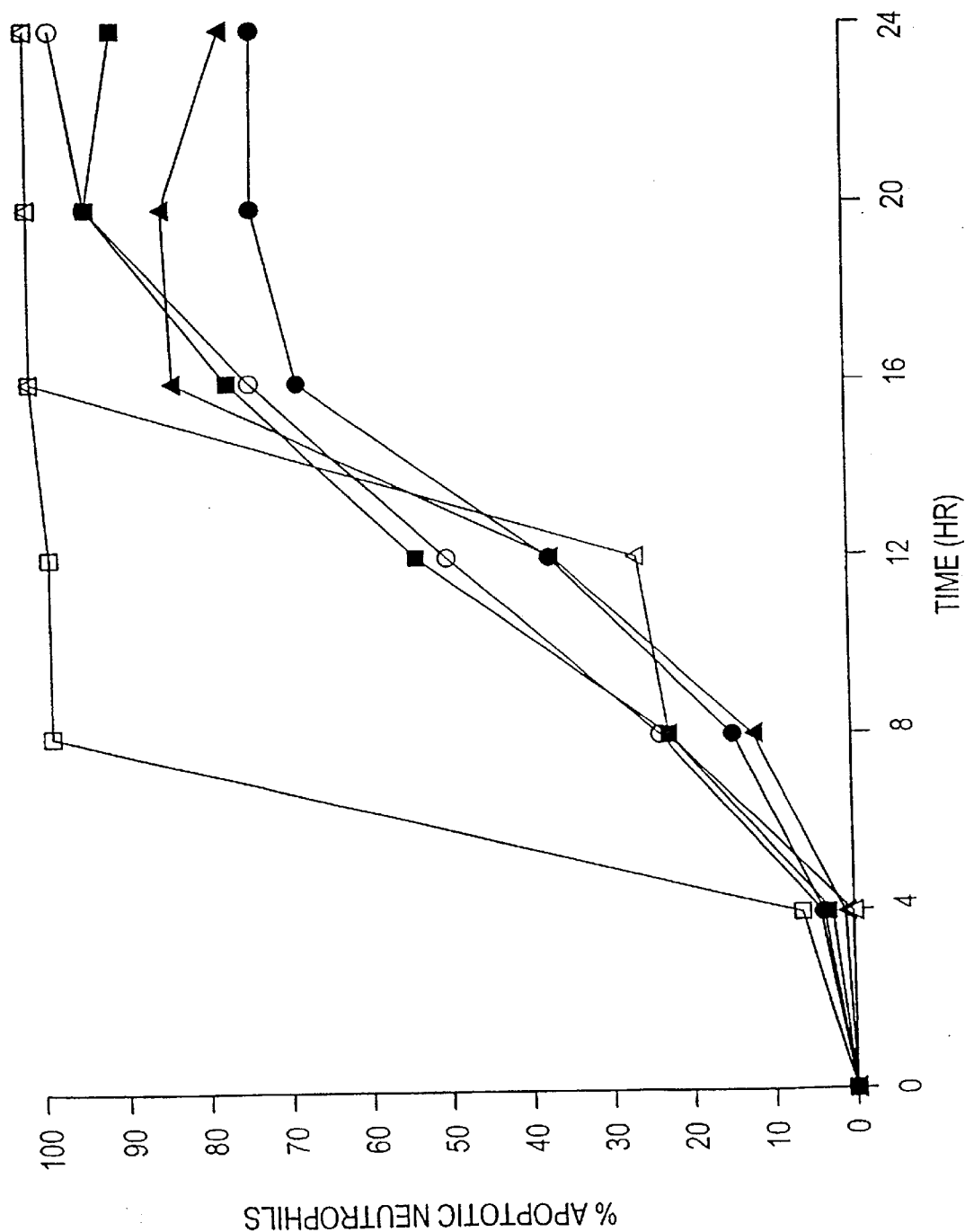
FIG. 9 shows tPA alone significantly reduced the rate of apoptosis and the percent apoptotic cells at 24 hours. Open circle, cells alone; closed circle, tPA alone; open square, PMA alone; closed square, fMLP alone; open triangle, tPA+PMA; and closed triangle, tPA+fMLP.

Rats that were treated with tPA (12 mg/Kg body weight, i.p.) had increased lung tPA levels (measured at 5 hours) compared to untreated rats. Rats treated with tPA (12 mg/Kg body weight, i.p.) had an approximately 80% reduction in lung leak compared to untreated rats given IL-1 intratracheally (FIG. 7). Lung leak in rats given L-arginine (440 mg/Kg body weight, i.p.) along with IL-1 was not different from lung leak in rats given IL-1 (FIG. 9). In contrast, rats given both tPA and IL-1 had the same number of lavage neutrophils and lung MPO activities as untreated rats given IL-1 intratracheally (Table 1). Consistent with the in vivo data of Example 2, tPA failed to abrogate neutrophil migration induced by an inflammatory stimulus in vivo (Table 1).

TABLE 1

Effect of tPA on lung lavage neutrophils (PMNs) and lung MPO activity in rats given IL-1 intratracheally.

| Treatment | Lung lavage PMNs (% total cells) | Lung lavage PMNs (total #, millions) | MPO in whole lung (U/gm left lung) |
|---|---|---|---|
| control* | 3 ± 1 | 0.003 ± 0.001 | 0.6 ± 0.2 |
| IL-1 | 95 ± 1⁺ | 2.9 ± 0.4⁺ | 11.2 ± 2.9⁺ |
| tPA + IL-1 | 95 ± 1⁺ ^ | 2.7 ± 0.4⁺ ^ | 11.1 ± 1.6⁺ ^ |

*mean ± SEM of six determinations.
⁺value significantly different (p < 0.05) from control value; mean ± SEM of ten determinations.
^ value not significantly different (p > 0.05) from value obtained for rats given IL-1 alone; mean ± SEM of six determinations.

Lung leak, lung myeloperoxidase (MPO) activity, and lung lavage neutrophil counts were increased in rats given IL-1 intratracheally compared to control rats that were given saline intratracheally. Giving tPA (12 mg/Kg body weight) intraperitoneally increased lung tPA concentration and reduced acute lung leak in rats given IL-1 intratracheally (p<0.01). Lung leak index for sham treatment was 0.040±0.001 (n=6), IL-1 treatment was 0.10±0.01 (n=10), and tPA+IL-1 treatment was 0.050±0.002 (n=6). In contrast, administering tPA did not change the IL-1 induced increases in lavage neutrophils (sham treatment was 3±1×10³ cells, IL-1 treatment was 2.9±0.4×10⁶ cells, and tPA+IL-1 treatment was 2.7±0.4×10⁶ cells) or lung MPO activity (sham treatment was 0.6±0.2 U/gm lung, IL-1 treatment was 11.2±2.9 U/gm lung, and tPA+IL-1 was 11.1±1.6 U/gm lung). We have demonstrated that IL-1 induced neutrophil-dependent lung injury can be modulated by tPA. Administration of intraperitoneal tPA increases lung tissue tPA levels and decreases acute lung injury, without reducing lung neutrophil infiltration in rats given IL-1α intratracheally. As the systemic administration of tPA resulted in a measurable increase in tPA concentration in the lung, inhibition of lung injury is probably due to an inhibitory effect of tPA on neutrophil $O_2^-$ production.

EXAMPLE 4

Plasminogen Activator's Anti-Inflammatory Effect on Macrophages

Chemiluminescence was used to measure the oxidative burst of rat alveolar macrophages (NR 8383 cells). Oxidant production was determined by luminol chemiluminescence measured using a luminometer (Lumistar, BMG Lab Technologies Inc., Durham, N.C.) (Archer et al. J. Appl. Physiol. 67:1912–21, 1989). Experiments were conducted in an opaque 96-well plate at 37° C. Suspensions of macrophages (100 μl of 5 million cells/ml) were plated in the presence or absence of tPA (100 μg/ml) 60 min prior to exposure to an activator (PMA, zymosan, or opsonized zymosan). Prior to the addition of activator, 200 μl of buffered luminol solution (0.1 μM) containing horseradish peroxidase (0.5 mg/ml) was added to each well and chemiluminescent light emission was determined (baseline was measured at time 0). Following addition of an activator, chemiluminescent light emission was measured every 10 min for two hours. The experiments were performed in triplicate. The assay has a detection limit of approximately 100 nM hydrogen peroxide.

Figure 8:
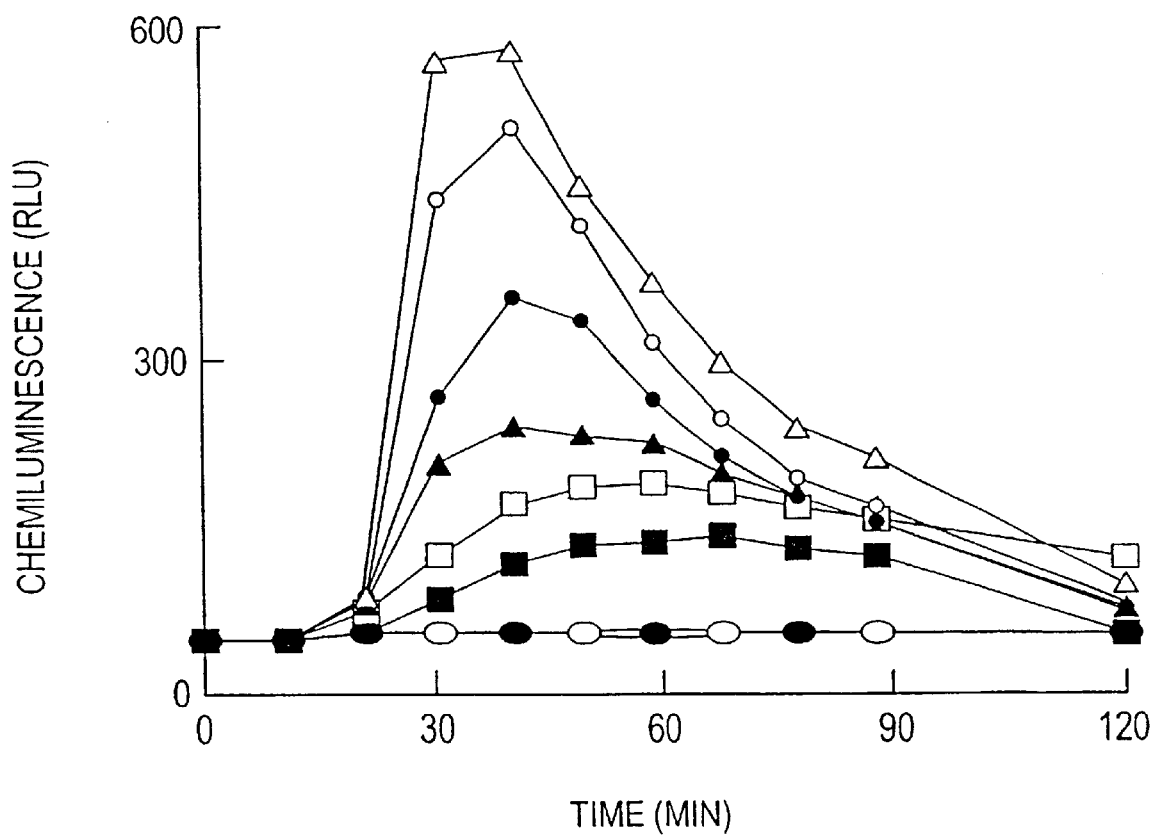
FIG. 8 shows tPA induced inhibition of oxidant production by a rat alveolar macrophage line. Cells were pretreated with tPA (100 µg/ml) or vehicle, and subsequently exposed to phorbol ester (PMA, 1.25 µg/ml), zymosan (ZMA, 60 µg/ml), or opsonized zymosan (opZMA, 60 µg/ml). Large open circle, control; large closed circle, tPA; open square, PMA; closed square, PMA+tPA; open triangle, ZMA; closed triangle, ZMA+tPA; small open circle, opZMA; and small closed circle, opZMA+tPA. Data represent mean values from triplicate estimations.

Addition of an activator resulted in an increase in oxidant production by the macrophages (FIG. 8). tPA reduced activator induced oxidant production, demonstrating that the ability of tPA to inhibit oxidant production is not selective for neutrophils but, instead extends to different types of leukocytes.

EXAMPLE 5
Evaluation of the Effect of Tissue Plasminogen Activator (tPA) on Neutrophil Apoptosis Neutrophils were isolated from the whole blood of a single, healthy, medication-free individual using venipuncture and methods previously described (Stringer et al., Inflammation 21:27–34, 1997). Cells ($1 \times 10^6$ cells/ml) were suspended in Krebs-Ringers-Phosphate-Dextrose (KRPD) buffer and equally divided between two tubes. To one tube, tissue plasminogen activator (tPA) was added to produce a final concentration of 100 $\mu$g/ml. Cell suspension (200 $\mu$l) was placed in each well of a 96-well microtiter plate and the plate was incubated (37° C., 5% $CO_2$) for 30 min. Following the incubation, phorbol myristate acetate (PMA, 1.25 $\mu$g/ml) or formyl-methionyl-leucyl-phenylalanine (fMLP, 5 $\mu$M) was added to wells so that the following conditions were met: cells alone, tPA alone, tPA+PMA, tPA+fMLP, PMA alone, or fMLP alone. The plate was then incubated again (37° C., 5% $CO_2$) for 30 min.

The percent apoptotic cells was determined at time 0 (immediately following incubation), then at 4, 8, 12, 16, 20, and 24 hr. At each time point, cells (25 $\mu$l) were removed from each well of the microtiter plate and placed into a glass tube with 1 $\mu$l of ethidium bromide/acridine orange (4 $\mu$g/ml each). Cells (10 $\mu$l) were then placed on a microscope slide with a cover slip. Cells were viewed under a microscope (100×) equipped with a fluorscein filter. For each assessment, cells (n=100) were counted and "scored" as either "live apoptotic", "live normal", "dead apoptotic", or "dead normal" (Duke et al. In: Current Protocols in Immunology, edited by Coligan et al., John Wiley & Sons, New York, pp. 3.17.1–3.17.33, 1995). The percent apoptotic cells was determined by adding the number of live and dead apoptotic cells.

tPA alone significantly reduced the rate of apoptosis and the percent apoptotic cells at 24 hours (FIG. 9). The rate and magnitude of apoptosis was significantly enhanced by PMA while fMLP had no effect. The addition of tPA significantly slowed the rate and reduced the magnitude of apoptosis in PMA-treated cells, and reduced the rate and magnitude of apoptosis in fMLP-treated cells.

While the present invention has been described in connection with what is presently considered to be practical and preferred embodiments, it is understood that the present invention is not to be limited or restricted to the disclosed embodiments but, on the contrary, is intended to cover various modifications and equivalent arrangements included within the scope of the appended claims.

Thus, it is to be understood that variations in the described invention will be obvious to those skilled in the art without departing from the novel and non-obvious aspects of the present invention, and such variations are intended to come within the scope of the claims below.

We claim:

1. A method of treating a subject with an inflammatory lung disease or condition comprising:

administering to a subject with an inflammatory lung disease or condition a therapeutically effective amount of a tissue plasminogen activator protein having anti-inflammatory activity, wherein a therapeutically effective amount is an amount of said tissue plasminogen activator (tPA) protein sufficient to reduce inflammation or inflammation-dependent lung damage in said subject.

2. The method of claim 1 wherein said inflammatory lung disease is selected from the group consisting of acute lung injury, acute respiratory distress syndrome, asthma, bronchitis, and cystic fibrosis.

3. The method of 2 where the inflammatory lung disease is acute respiratory distress syndrome (ARDS).

4. The method of claim 1 wherein said tissue plasminogen activator protein is administered via oral, topical, inhalation or parental administration.

5. The method of claim 4 wherein said tissue plasminogen activator protein is administered via inhalation.

6. The method of claim 5 wherein said tissue plasminogen activator protein is administered via intravascular infusion.

7. The method of claim 6 where said tissue plasminogen activator protein is administered by use of an aerosol composition.

* * * * *